(12) United States Patent
Uutela et al.

(10) Patent No.: US 10,172,526 B2
(45) Date of Patent: Jan. 8, 2019

(54) SYSTEM AND METHOD OF DETECTION OF SENSOR REMOVAL IN A MONITORING SYSTEM

(71) Applicant: General Electric Company, Schenectady, NY (US)

(72) Inventors: Kimmo Henrik Uutela, Helsinki (FI); Matti Veli Tapani Huiku, Helsinki (FI); Emma Elina Ikonen, Helsinki (FI)

(73) Assignee: General Electric Company, Schenectady, NY (US)

( * ) Notice: Subject to any disclaimer, the term of this patent is extended or adjusted under 35 U.S.C. 154(b) by 224 days.

(21) Appl. No.: 15/140,656

(22) Filed: Apr. 28, 2016

(65) Prior Publication Data

US 2017/0311818 A1    Nov. 2, 2017

(51) Int. Cl.
| | |
|---|---|
| *A61B 5/01* | (2006.01) |
| *A61B 5/0205* | (2006.01) |
| *A61B 5/145* | (2006.01) |
| *A61B 5/0402* | (2006.01) |
| *A61B 5/11* | (2006.01) |
| *A61B 5/00* | (2006.01) |

(52) U.S. Cl.
CPC ............ *A61B 5/02055* (2013.01); *A61B 5/01* (2013.01); *A61B 5/0402* (2013.01); *A61B 5/11* (2013.01); *A61B 5/1123* (2013.01); *A61B 5/14542* (2013.01); *A61B 5/6801* (2013.01); *A61B 5/7282* (2013.01); *A61B 5/746* (2013.01); *A61B 2560/0233* (2013.01)

(58) Field of Classification Search
CPC ..... A61B 5/02055; A61B 5/7282; A61B 5/01; A61B 5/6801; A61B 5/11; A61B 5/0402; A61B 5/14542; A61B 5/746
See application file for complete search history.

(56) References Cited

U.S. PATENT DOCUMENTS 6,421,554 B1    7/2002   Lee et al.
2015/0335877 A1*  11/2015  Jeffery ................. A61N 1/0492
                                                       607/139

FOREIGN PATENT DOCUMENTS

WO          2012077113 A2    6/2012

* cited by examiner

*Primary Examiner* — Rex R Holmes
(74) *Attorney, Agent, or Firm* — Andrus Intellectual Property Law, LLP

(57) ABSTRACT

The system and method of the present application includes a physiological sensor and a motion sensor connected to a patient. The physiological sensor detects patient connection to the sensor and collects a physiological signal while connected. When the physiological sensor is disconnected, the motion sensor data is analyzed. Patterns of sensor connection and patient movement typical for nurse initiated removal compared to accidental or patient initiated removals are created. The alarm protocol may be modified if the disconnection is due to patient movement. The detected movement patterns may include movement measurements that are close to the sensor that detects how the actual disconnection happens, or general movement information for the patient such as whether the patient has been still or has moved before the sensor gets disconnected. By using this information to classify the reason of the sensor removal, a more relevant alarm may be generated.

11 Claims, 4 Drawing Sheets

SYSTEM AND METHOD OF DETECTION OF SENSOR REMOVAL IN A MONITORING SYSTEM

FIELD

The present disclosure generally relates to medical devices. More specifically, the present disclosure relates to monitoring devices for monitoring a patient's physiology and health status.

BACKGROUND

Sensor removal in monitoring devices and systems disrupts patient monitoring, and is often accompanied by an alarm. The sensor removal is sometimes purposeful, for example, for stopping the monitoring or moving the sensor to a different location on the patient. Conversely, accidental sensor removal occurs, for example, when the sensor drops off of a patient due to patient action and/or movement. Intentional sensor removal alarms are common in the intensive care unit (ICU) environment, and are especially common in blood oxygen saturation (SPO2) and electrocardiogram (ECG) measurements. Often, such removals and the resulting alarms are not considered relevant by users. Irrelevant alarms cause alarm fatigue in practitioners and medical professionals, and decrease appropriate responses to relevant accidental, unintentional sensor removal alarms. Current systems include sensor removal alarms that may be silenced before they occur or acknowledged by the user after they have alarmed. However, this typically affects all alarms and is therefore not an ideal solution.

SUMMARY

The system and method of the present application includes a physiological sensor and a motion sensor, such as an accelerometer, connected to a patient. The physiological sensor detects patient connection to the sensor and collects a physiological signal while connected. When the physiological sensor is disconnected, the motion sensor data is analyzed for a predetermined period prior to disconnection. Based on previous measurements, patterns of sensor connection and patient movement typical for nurse initiated removal compared to accidental or patient initiated removals are created. The alarm generated by the monitor may also be modified if the disconnection of the sensor is due to patient movement.

The detected movement patterns may include movement measurements that are close to the sensor that detects how the actual disconnection happens, or general movement information for the patient such as whether the patient has been still or has moved before the sensor gets disconnected. By using this information to classify the reason of the sensor removal, a more relevant alarm may be generated.

In one aspect of the present application, a monitoring system for monitoring a patient, comprises a physiological sensor attached to the patient, wherein the physiological sensor collects physiological data from the patient, a motion sensor attached to the patient, wherein the motion sensor collects movement data from the patient, a monitoring device, wherein the monitoring device receives the physiological data and movement data from the physiological sensor, and further wherein the monitoring device detects when the physiological sensor fails to collect the physiological data and then analyzes the movement data collected for a predetermined time period prior to the physiological sensor failing to collect the physiological data, wherein an alarm protocol is modified by the monitoring device when the analyzed movement data collected for the predetermined time period indicates the intentional removal of the physiological sensor. The alarm protocol may be modified by any of delaying the generation of an alarm, changing an audible sound of the alarm, modifying the display of the alarm and creating a new alarm priority.

In another aspect of the present application a computerized method of detecting sensor removal in a monitoring system, comprises collecting physiological data from a patient with a physiological sensor, collecting movement data from the patient with a motion sensor, receiving the physiological data and movement data from the physiological sensor in a monitoring device, and further detecting with the monitoring device when the physiological sensor fails to collect the physiological data, analyzing with the monitoring device the movement data collected for a predetermined time period prior to the physiological sensor failing to collect the physiological data, and modifying an alarm protocol when the analyzed movement data indicates the intentional removal of the physiological sensor.

In yet another aspect of the present application, a monitoring system for detection of sensor removal when monitoring a patient, comprises a combined sensor unit attached to the patient, wherein the combined sensor unit includes both a physiological sensor and a motion sensor, wherein the physiological sensor collects physiological data from the patient, and the motion sensor collects movement data from the patient, a monitoring device, wherein the monitoring device receives the physiological data and movement data from the combined sensor unit, and further wherein when the combined sensor unit stops collecting physiological data, the monitoring device analyzes both the physiological data and the movement data for a predetermined time period prior to the physiological sensor failing to collect the physiological data, and further wherein the monitoring device compares the analyzed physiological data and movement data to a database of a plurality of patterns of past recorded data, wherein the plurality of patterns all represent an intentional removal of the combined sensor unit, and an alarm, wherein when the analyzed physiological data and movement data match any of the plurality of patterns, the alarm protocol is modified. The alarm protocol may be modified by any of delaying the generation of an alarm, changing an audible sound of the alarm, modifying the display of the alarm and creating a new alarm priority.

DETAILED DESCRIPTION

In the present description, certain terms have been used for brevity, clearness and understanding. No unnecessary limitations are to be applied therefrom beyond the requirement of the prior art because such terms are used for descriptive purposes only and are intended to be broadly construed. The different systems and methods described herein may be used alone or in combination with other systems and methods. Various equivalents, alternatives and modifications are possible within the scope of the appended claims. Each limitation in the appended claims is intended to invoke interpretation under 35 U.S.C. § 112, sixth paragraph, only if the terms "means for" or "step for" are explicitly recited in the respective limitation.

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

The technical effect of the system and method of the present application is to improve the function and operation of current monitoring systems and methods to include more detailed and useful information for a user. Specifically, the system and method improves the ability of the system to detect unintentional disconnection of physiological sensors due to patient movement as opposed to intentional disconnection by a user, such as by a nurse or other medial professional.

In practice, sensor removal alarms are most common with SpO2 and ECG measurements, and the system and method will assist with identifying the cause of sensor disconnection while taking those measurements and also with other measurement parameters such as, but not limited to, NIBP/Inv BP, EEG/Entropy/BIS, and temperature, among others. By classifying reasons for the sensor removal, the purposeful alarms for the nurse or other user may be modified to alarm a longer alarm delay, different message, lower priority, or only informal message, while giving a prompt alarm if the sensor is accidentally removed. Thus the irrelevant alarms are less frequent or easier to separate from relevant ones by a user.

Figure 1:
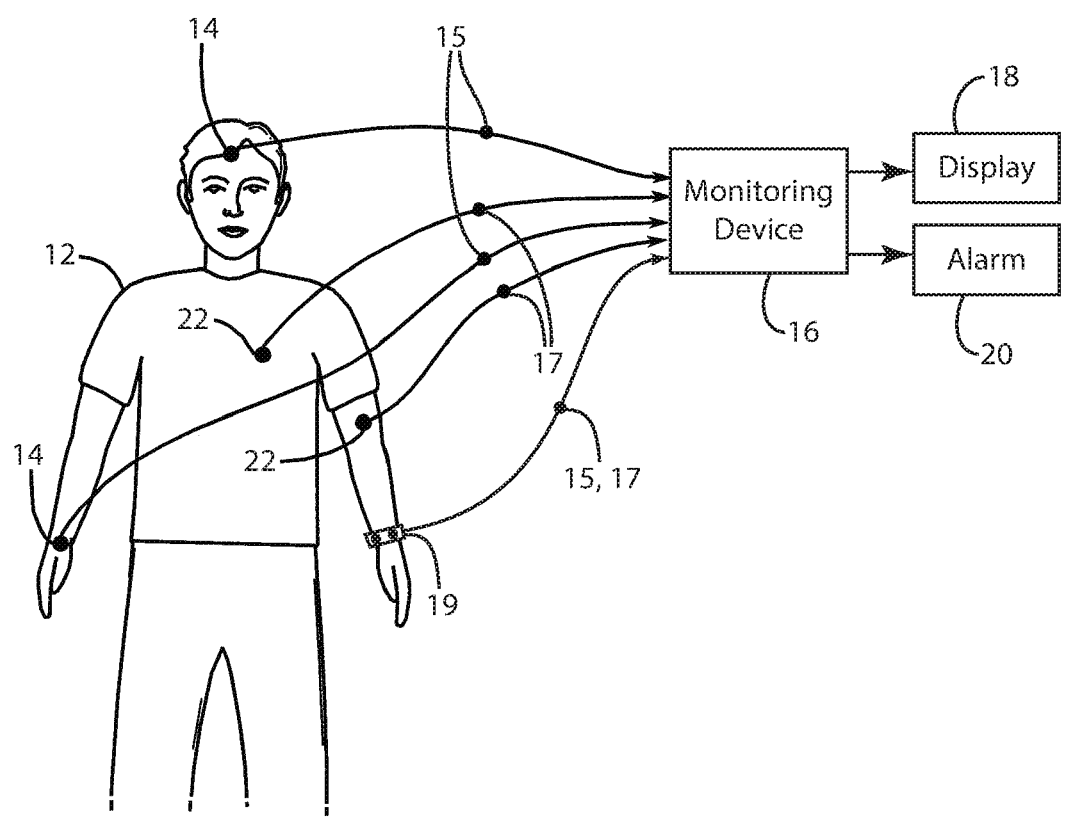
FIG. 1 is a schematic diagram of a system illustrating an embodiment of the present application.

FIG. 1 illustrates a system 10 of the present application. Here, a patient 12 is being monitored for a physiological parameter, and therefore has at least one physiological sensor 14 affixed to his/her body. Of course, depending upon the physiological parameter being monitored, the patient 12 may have any number of physiological sensors 14 collecting and sending a physiological data set 15 to the monitoring device 16. Further in this system 10 of the present application illustrated in FIG. 1, the patient 12 is also being monitored for movement with a motion sensor 22. Again, depending on the type of movement to be analyzed, and the level of movement tolerance desired, the patient 12 may have one or several motion sensors 22 attached to various points on his/her body. The motion sensor 22 may be any motion sensor known in the art that may be attached to a person and detect motion. Such motion sensors 22 may include an accelerometer, gyroscope, magnetometer, and/or compass. Again, this is only a partial list of potential motion sensors 22, and should not limit the type of sensor used in the motion sensor 22 of the present application. The motion sensors 22 send a set of movement data 17 to the monitoring device 16. In other embodiments, a combined sensor unit 19, which includes both a physiological sensor 14 and a motion sensor 22 are combined in a single, attachable sensor unit, wherein both the physiological sensor 14 and the motion sensor 22 are simultaneously attached and/or removed from the patient 12. Such a combined sensor unit will provide both the physiological data 15 and the movement data 17 to the monitoring device 16 simultaneously. As stated previously, the physiological sensor 14 in the system 10 contemplated, may collect any physiological data set 15 that the system 10 is intended to collect (e.g., SpO2, ECG, temperature, BP). The monitoring device 16 may be any device capable of collecting physiological data 15 and movement data 17, and further configured to carry out a software application that will analyze and compare the data sets 15, 17 in order to provide an appropriate alarm signal to an alarm device 20 or message on a display 18 for a user. The monitoring device 16 may be a bedside monitor, a handheld monitor, a unit configured at a doctor or nurse station, or any other monitoring device 16 utilized for monitoring patients 12. The monitoring device 16 will output the results of the monitoring of the physiological data 15 and the movement data 17 to a user configured to receive both the display 18 and/or the alarm 20, which will be discussed in further detail below.

It should further be noted that all of the sensors 14, 22 and combined sensors 19 above may communicate wirelessly or in a wired fashion with the monitoring device 16 and/or with any other data collection device (not shown) utilized to collect the physiological and movement data 15, 17 for the monitoring device 16. It is further contemplated that collection devices (not shown) may be utilized to more easily collect the data 15, 17 and send the data 15, 17 to the monitoring device 16. Such collection devices may be worn by the patient or be part of a home monitoring system. It is also contemplated that these motion sensors be implemented in another portion of a physiological collection system existing or contemplated. For example, it is contemplated that the patient 12 may be utilizing a collection system that has modular physiological sensors with batteries, and collection devices that can be worn by the patient 12 that also include power sources, aggregators, and other components that would facilitate a full remote collection device that can be worn by a patient. In such cases, it is contemplated that the motion sensors 22 in a combined sensor unit 19 may be implemented near a battery, another collection device or aggregator, or some sort of collection hub in such systems. In such cases, the motion sensor 22, in a combined sensor unit 19 setting, would detect the motion of the physiological sensor or other component of the system.

Figure 2:
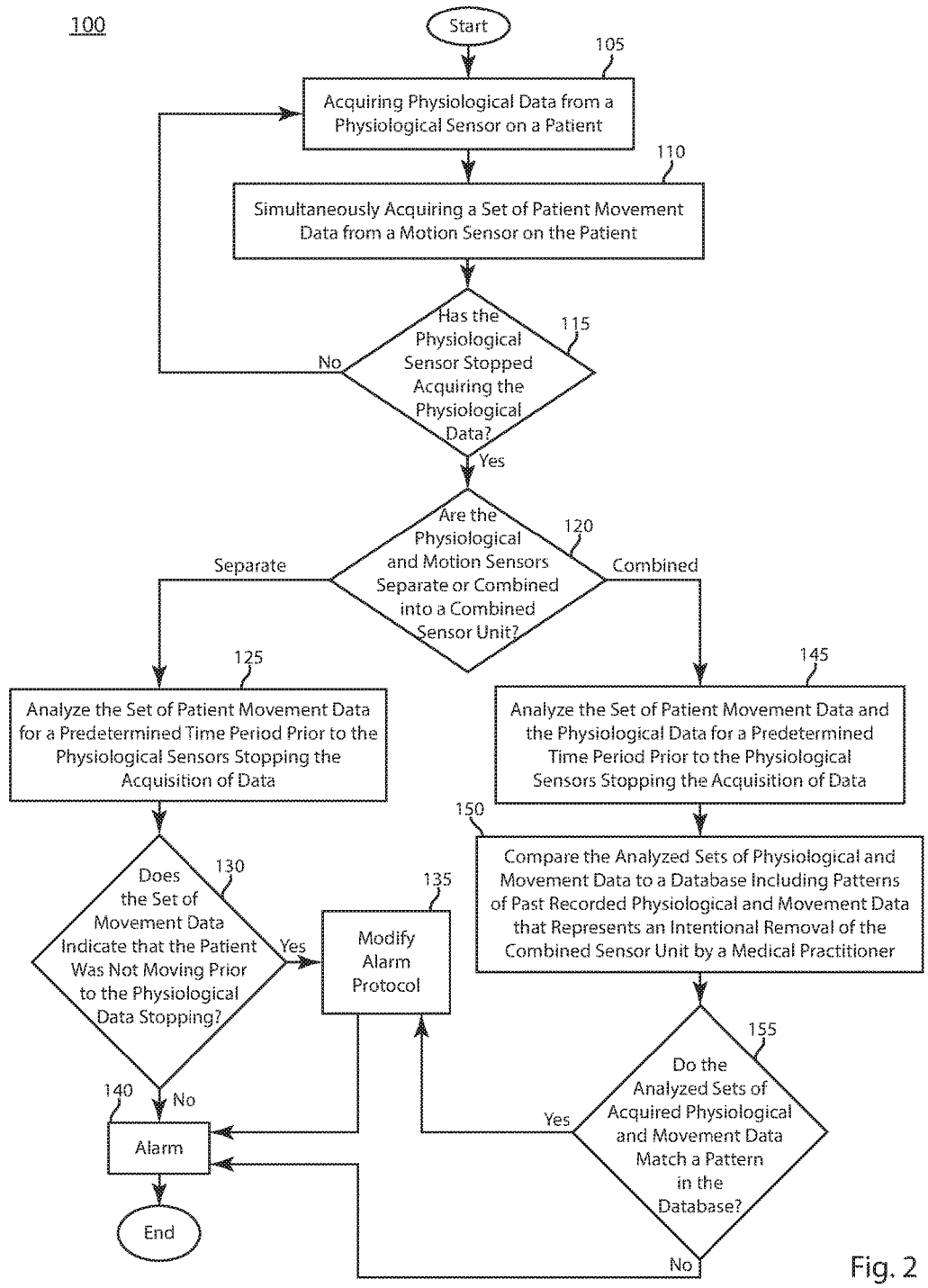
FIG. 2 is a flowchart of a method illustrating an embodiment of the present application.

Now referring to FIG. 2, a method 100 of the present application is illustrated. In step 105, physiological data is acquired from a physiological sensor configured on a patient. As stated previously, the physiological data may include any physiological parameters desired to be collected from a patient, including, but not limited to, SpO2, ECG, temperature, BP, and in step 110, a set of patient movement data is simultaneously acquired from a motion sensor configured on a patient. In another embodiment, a combined sensor unit including both a physiological and motion sensor may be utilized, and such a combined sensor may be used in combination with an embodiment using separate sensors, as described above. In step 115, as long as the physiological sensor continues to acquire the physiological data, the method will repeat through steps 105 and 110 in a loop, collecting both the physiological and motion data from the patient 12. However, if the physiological sensor stops acquiring physiological data due to disconnection of the physiological sensor, or through failure of the same, then the method continues to step 120. In step 120, if the physiological and motion sensors are separate sensors, and not a combined sensor unit, then in step 125, the set of patient movement data is analyzed for a predetermined time period prior to the physiological sensor stopping the acquisition of data. In other words, the method of the present application will look backward at the set of patient movement data from the time the data acquisition stopped, for a predetermined time period. The predetermined time period may be selected by a user, or a default predetermined time period setting may be utilized by the method. It is contemplated that in one embodiment, this predetermined time period will be one that is measured in seconds in order to show movement of the patient directly preceding the physiological sensors no longer acquiring physiological data. However, shorter and longer predetermined time periods are contemplated.

In step 130, when the set of movement data indicates that the patient was not moving during the predetermined time period prior to the physiological data collections stopping, this will indicate that the patient was still during the removal of the physiological sensors, and that such lack of movement indicates that a nurse or other medical practitioner was actively, intentionally and purposefully removing the physiological sensors from the patient. In this case, the method 100 moves to step 135, where the method will then modify the alarm protocol, so as not to send a known alarm that will indicate that a sensor has accidentally or unintentionally fallen off of the patient. As discussed previously, the modified alarm protocol may include delaying the generation of the alarm, changing the audible sound of the alarm, changing the type of alarm indicator that is displayed, creating a lower priority alarm level and/or alarming by delivering a visual message to a user through a display is contemplated. Other modifications to either the alarm generated by the monitoring device or communicated from the monitoring device are also contemplated as being within the scope of the present disclosure. Additionally, it is contemplated that the monitoring device could either generate the alarm itself or that the monitoring device could generate an alarm signal to a separate display or a separate alarm device. The modification to the alarm protocol would apply to each type of configuration. Then in step 140, the modified alarm protocol is delivered either from the monitoring device to the user or to the user through any one of a variety of alarm devices, such as a visual display, audible sound generator or any other type of device that is known as being capable of delivering an alarm to a user.

Still referring to FIG. 2, if in step 120 the physiological and motion sensors are embodied in a combined sensor unit, then in step 145, the set of patient movement data and the physiological data are analyzed for predetermined time prior to the physiological sensors no longer acquiring data. In step 150, these analyzed combined sets of physiological and movement data are compared to a preexisting database that includes patterns of past recorded combined physiological and movement data that represent an intentional removal of the combined sensor unit by a medical practitioner so that the sequence of events leading up to the sensor disconnection may be classified. In other words, exemplary sets of combined physiological and movement data that are known to correspond to intentional removal of sensors from a patient are collected and stored in this database, so that current analyzed sets of combined data may be compared to the patterns in the database for possible matches. In step 155, if the analyzed sets of combined physiological and movement data match a pattern in the database, then the method moves on to step 135, wherein the alarm protocol is modified as described above, indicating an intentional removal of the physiological sensors. The collected and analyzed combined set of data would then be added to the database to create higher database accuracy, and so that the database can identify and adapt to different and varying types of movement. If in step 155, the analyzed sets of combined physiological and movement data do not match a pattern in the database, then a normal alarm is sounded in step 140. After step 140, the method ends. Referring back to step 135, and step 155, if the analyzed combined sets of acquired physiological and movement data do indeed match a pattern in the database, an additional modification alarm protocol for such a match may include an informational message instead of an audible alarm displayed for a user of the system on the display of the monitoring device. Furthermore, the alarm protocol modification step 135 may also learn which alarm modifier to use based on the movement characteristics of the patent as described above. As can be understood by the above description, the system and method of the present disclosure modifies the alarm protocol when the analyzed data from motion sensor indicates that relatively no movement of the patient occurred during the predetermined time period prior to disruption in the data received from the physiological sensor.

Still referring to FIG. 2, the method 100 may still be carried out using both separate physiological and motion sensors, as well as combined physiological and motion sensors in a combined sensor unit. In other words, after step 120, if both types of sensor embodiments exist in a system, the method may split and carry out both paths of the method simultaneously after step 120.

Figure 3:
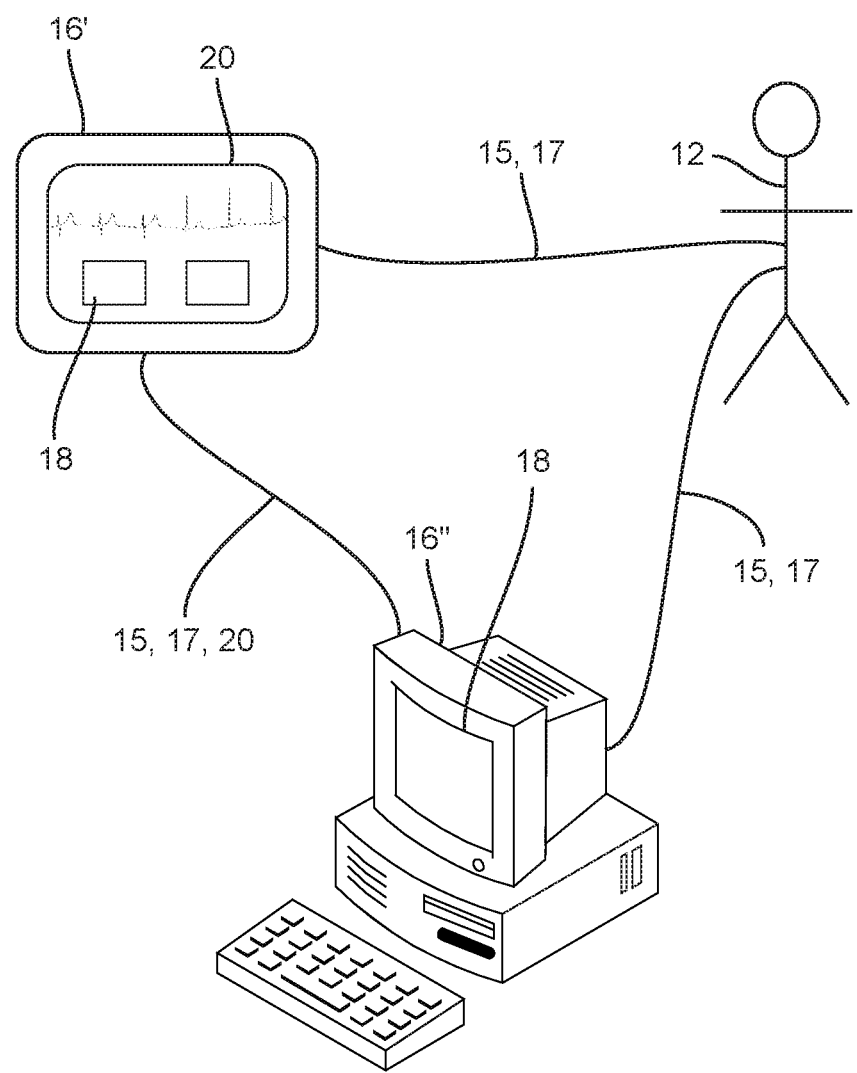
FIG. 3 is a schematic diagram of a system illustrating an embodiment of the present application.

FIG. 3 also illustrates a schematic diagram the system 10 of the present application. Here, two separate embodiments of a monitoring device 16 are illustrated, one being exemplary of a bedside ECG monitor 16', and the other exemplary of a PC, laptop or other desktop monitor 16" that may be positioned at nurses' station or for some type of medical practitioner. In one embodiment, physiological and movement data sets 15, 17 from the patient 12 may be transmitted to either of the monitoring devices 16, or to one of the monitoring devices 16 and the physiological and movement data sets 15, 17 as well as any alarms 20 may be transmitted between the monitoring devices 16. In one exemplary embodiment, the physiological and movement data sets 15, 17 are transmitted to one monitoring device 16' having a display 18, such that an audio or visual alarm 20 may be displayed on the monitoring device 16, and the data sets 15, 17 as well as the alarm 20 are transmitted to a second monitoring device 16" that may be positioned at a nurse's station, or some other user remote location.

Figure 4:
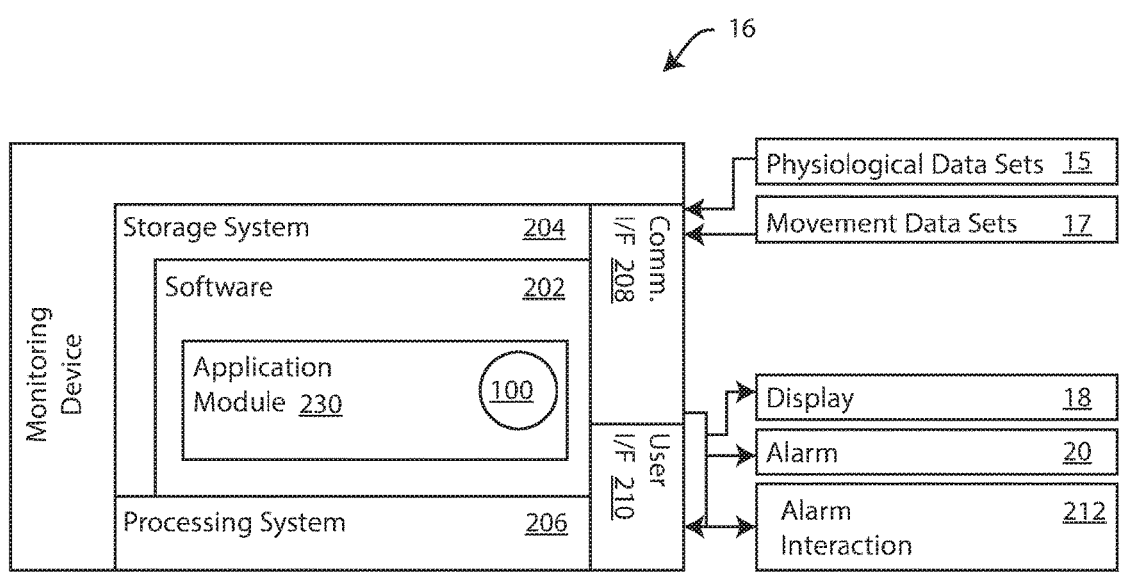
FIG. 4 is a schematic diagram of a monitoring device illustrating an embodiment of the present application.

FIG. 4 is a system diagram of an exemplary embodiment of a monitoring device 16 for monitoring a patient 12 as described above. In exemplary embodiments, the monitoring device 16 may be used to implement embodiments of the method 100 as exemplarily described above with respect to FIG. 2. The monitoring device 16 generally includes a computing system having a processing system 206, storage system 204, software 202, communication interface 208 and a user interface 210. The processing system 206 loads and executes software 202 from the storage system 204, including an application module 230. When executed by the monitoring device 16, application module 230 directs the processing system 206 to operate as described herein in further detail in accordance with the method 100 as described above with respect to FIG. 2.

Although the monitoring device 16 as depicted in FIG. 4 includes one application module 230 in the present example, it should be understood that one or more modules could provide the same operation. Similarly, while description as provided herein refers to a monitoring device 16 and a processing system 206, it is to be recognized that implementations of such systems can be performed using one or more processors, which may be communicatively connected, and such implementations are considered to be within the scope of the description.

The processing system 206 can include a microprocessor and other circuitry that retrieves and executes software 202 from storage system 204. Processing system 206 can be implemented within a single processing device but can also be distributed across multiple processing devices or subsystems that cooperate in executing program instructions. Examples of processing system 206 include general purpose central processing units, application specific processors, and logic devices, as well as any other type of processing devices, combinations of processing devices, or variations thereof.

The storage system 204 can include any storage media readable by processing system 206, and capable of storing software 202. The storage system 204 can include volatile and non-volatile, removable and non-removable media implemented in any method or technology for storage of information, such as computer readable instructions, data structures, program modules, or other data. Storage system 204 can be implemented as a single storage device but may also be implemented across multiple storage devices or sub-systems. Storage system 204 can further include additional elements, such a controller capable of communicating with the processing system 206.

Examples of storage media include random access memory, read only memory, magnetic discs, optical discs, flash memory, virtual and non-virtual memory, magnetic sets, magnetic tape, magnetic disc storage or other magnetic storage devices, or any other medium which can be used to store the desired information and that may be accessed by an instruction execution system, as well as any combination or variation thereof, or any other type of storage medium. In some implementations, the storage media can be a non-transitory storage media.

User interface 210 can include a mouse, a keyboard, a voice input device, a touch input device for receiving a gesture from a user, a motion input device for detecting non-touch gestures and other motions by a user, and other comparable input devices and associated processing elements capable of receiving user input from a user. In embodiments, the user interface 210 operates to present and/or to receive information to/from a user of the monitoring device 16. Output devices such as a video display 18 or graphical display can display an interface further associated with embodiments of the system 10 and method 100 as disclosed herein. Audible alarm devices 20, such as speakers, as well as printers, haptic devices and other types of output devices may also be included in the user interface 210.

As described in further detail herein, the monitoring device 16 receives and transmits data through the communication interface 208. In embodiments, the communication interface 208 operates to send and/or receive data to/from other devices to which the monitoring device 16 is communicatively connected, including other monitoring devices 16. In the monitoring device 16, physiological data sets 15 are received from a patient 12 and/or may also be transmitted to or from another monitoring device 16. As described above, the monitoring device 16 also receives movement data sets 17 from a patient 12 and/or may also be transmitted to or from another monitoring device 16, which is all exemplarily stored on one or more computer readable media. The monitoring device 16 executes the application module 230 exemplarily to carry out an embodiment of the method 100 as described herein.

The monitoring device 16 analyzes the physiological and movement data 15, 17 in order to identify intentional versus unintentional removal of the physiological sensors 14 as described above. The user interface 210 also provides an alarm 20 to a user, utilizing either an audio or visual alarm as noted above, and alarm interaction 212 allows a user to likewise receive the alarm as well as modify turn off, or delay an alarm as needed.

The functional block diagrams, operational sequences, and flow diagrams provided in the Figures are representative of exemplary architectures, environments, and methodologies for performing novel aspects of the disclosure. While, for purposes of simplicity of explanation, the methodologies included herein may be in the form of a functional diagram, operational sequence, or flow diagram, and may be described as a series of acts, it is to be understood and appreciated that the methodologies are not limited by the order of acts, as some acts may, in accordance therewith, occur in a different order and/or concurrently with other acts from that shown and described herein. For example, those skilled in the art will understand and appreciate that a methodology can alternatively be represented as a series of interrelated states or events, such as in a state diagram. Moreover, not all acts illustrated in a methodology may be required for a novel implementation.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

As described above, the system and method is configured to improve the operation of current systems and computers implementing those systems such that the monitoring system may be able to distinguish between intentional and unintentional sensor removal through patient motion detection.

In the foregoing description, certain terms have been used for brevity, clearness, and understanding. No unnecessary limitations are to be inferred therefrom beyond the requirement of the prior art because such terms are used for descriptive purposes and are intended to be broadly construed. The different configurations, systems, and method steps described herein may be used alone or in combination with other configurations, systems and method steps. It is to be expected that various equivalents, alternatives and modifications are possible within the scope of the appended claims.

We claim:

1. A monitoring system for monitoring a patient, comprising:
    a physiological sensor attached to the patient, wherein the physiological sensor collects physiological data from the patient;
    a motion sensor attached to the patient, wherein the motion sensor collects movement data from the patient; and
    a monitoring device, wherein the monitoring device receives the physiological data from the physiological sensor and the movement data from the motion sensor, and further wherein the monitoring device detects when the physiological sensor fails to collect the physiological data and then analyzes the movement data collected for a predetermined time period prior to the physiological sensor failing to collect the physiological data,
wherein the monitoring device modifies an alarm protocol when the analyzed movement data collected for the predetermined time period indicates the intentional removal of the physiological sensor.

2. The monitoring system of claim 1, wherein the intentional removal of the physiological sensor is indicated by relatively no movement of the patient during the predetermined time period.

3. The monitoring system of claim 1, wherein the physiological sensor is a blood-oxygen saturation (SpO2) sensor.

4. The monitoring system of claim 1, wherein the physiological sensor is an electrocardiogram (ECG) sensor.

5. The monitoring system of claim 1, further comprising a combined sensor unit attached to the patient, wherein the combined sensor unit includes both the physiological sensor and the motion sensor.

6. The monitoring system of claim 5, wherein when the combined sensor unit stops collecting physiological data, the monitoring device analyzes both the physiological data and the movement data for the predetermined time period.

7. The monitoring system of claim 6, wherein the monitoring device compares the analyzed physiological data and movement data to a database of a plurality of patterns of past recorded data, wherein the plurality of patterns all represent an intentional removal of the combined sensor unit.

8. The monitoring system of claim 7, wherein when the analyzed physiological data and movement data match any of the plurality of patterns, the alarm protocol is modified.

9. The monitoring system of claim 1, wherein the alarm protocol may be modified by any of delaying the generation of an alarm, changing an audible sound of the alarm, modifying the display of the alarm and creating a new alarm priority.

10. The monitoring system of claim 1, further comprising a display, wherein the display may deliver a visual modified alarm message.

11. A monitoring system for detection of sensor removal when monitoring a patient, comprising:
a combined sensor unit attached to the patient, wherein the combined sensor unit includes both a physiological sensor and a motion sensor, wherein the physiological sensor collects physiological data from the patient, and the motion sensor collects movement data from the patient;
a monitoring device, wherein the monitoring device receives the physiological data and movement data from the combined sensor unit, and further wherein when the combined sensor unit stops collecting physiological data, the monitoring device analyzes both the physiological data and the movement data for a predetermined time period prior to the physiological sensor failing to collect the physiological data, and further wherein the monitoring device compares the analyzed physiological data and movement data to a database of a plurality of patterns of past recorded data, wherein the plurality of patterns all represent an intentional removal of the combined sensor unit; and
an alarm device, wherein when the analyzed physiological data and movement data match any of the plurality of patterns, an alarm protocol for the alarm device is modified.

* * * * *